United States Patent [19]

Kroening et al.

[11] Patent Number: 4,934,191

[45] Date of Patent: Jun. 19, 1990

[54] METHOD FOR ELECTROMAGNETIC ULTRASONIC CONVERSION FOR MONITORING THE FILL LEVEL AND BUBBLE FORMATION IN ENCLOSURES CONTAINING LIQUID

[75] Inventors: Michael Kroening, Roettenbach; Ernst Loehr, Alzenau; Albin Walleser, Frankfurt; Gerhard Huebschen, Saarlouis; Wilhelm Repplinger, Dilingen; Hans-Juergen Salzburger, Neunkirchen, all of Fed. Rep. of Germany

[73] Assignee: Siemens Aktiengesellschaft, Munich, Fed. Rep. of Germany

[21] Appl. No.: 248,966

[22] Filed: Sep. 26, 1988

[30] Foreign Application Priority Data

Sep. 24, 1987 [DE] Fed. Rep. of Germany ....... 3732219

[51] Int. Cl.$^5$ ............................................. G01N 29/00
[52] U.S. Cl. ....................................... 73/592; 73/19.1; 376/258
[58] Field of Search ............... 73/15, 290 V, 597, 643, 73/19, 592; 367/908; 376/245, 258

[56] References Cited

U.S. PATENT DOCUMENTS

| H608 | 3/1989 | Goolsby | 73/290 V |
|---|---|---|---|
| 3,246,516 | 4/1966 | Maropis | 73/290 V |
| 3,656,134 | 4/1972 | Brown | |
| 4,144,517 | 3/1979 | Baumoel | 73/290 V |
| 4,203,324 | 5/1980 | Baumoel | 367/908 |
| 4,320,659 | 3/1982 | Lynnworth et al. | 73/290 V |

FOREIGN PATENT DOCUMENTS

| 0053068 | 6/1982 | European Pat. Off. |
| 2076536 | 12/1981 | United Kingdom |
| 2097923 | 11/1982 | United Kingdom |
| 1167185 | 5/1986 | United Kingdom |

OTHER PUBLICATIONS

Maxfield, B. W. et al., "The Design and Use of Electromagnetic Acoustic Wave Transducers" Materials Evaluation (41), Nov. 1983, pp. 1399-1408.

Japanese Patents, vol. 10, No. 305 (P-507) [2361] Oct. 17, 1986; JP-A61120020 (Hitachi Ltd.), 7/6/86; Abstract & Figures are pertinent.

Ultrasonics Symposium, IEEE 1979, "Liquid Level Measurements Using Longitudinal, Shear, Extensional & Torsional Waves"; L. C. Lynnworth; pp. 376-379; and FIG. 2 are pertinent.

*Primary Examiner*—Jerry W. Myracle
*Attorney, Agent, or Firm*—Herbert L. Lerner; Laurence A. Greenberg

[57] ABSTRACT

A method for electromagnetic ultrasonic conversion includes exerting dynamic-mechanical forces upon particles of an electrically conductive material of a test sample by superimposing quasi-static magnetic and electromagnetic high-frequency fields of a transmission converter for generating ultrasonic vibrations when transmitting. Electrical fields are induced by waves arriving in the test sample resulting in vibrations of the particles of material inductively affecting the fields of a receiver converter when receiving. The excitation of the vibrations when transmitting and the induction of electrical fields when receiving are effected by Lorentz and magnetic forces as well as by magnetostriction forces if the test sample is ferromagnetic. Fill level and bubble formation are monitored in enclosures in the form of containers and pipelines for liquid, by coupling a transmission converter and a receiver converter to an enclosure wall. Ultrasonic vibrations are generated in the wall inducing echo signals differing by amplitude and/or phase in the receiver converter, depending on whether the interior of the enclosure contains liquid, liquid containing steam or gas bubbles, or only a fluid in the form of vapor or gas, while reflecting the signals on the inner boundary surface of the wall or striking a reflector after entering the liquid and traveling a distance therein, and reflecting the signals back from the reflector through the fluid and through the wall to the receiver converter.

10 Claims, 2 Drawing Sheets

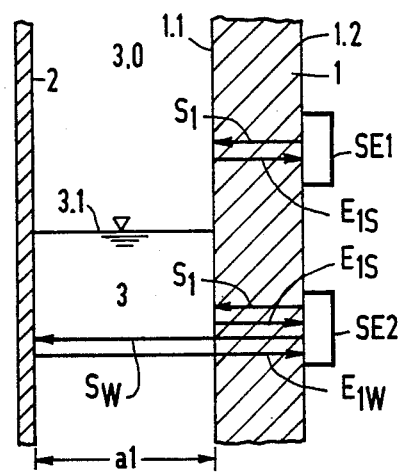
FIG 1
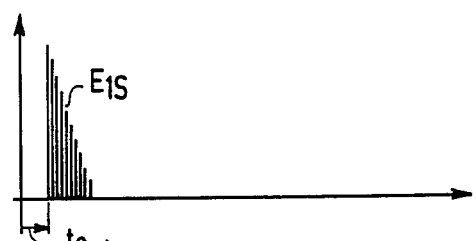
FIG 2
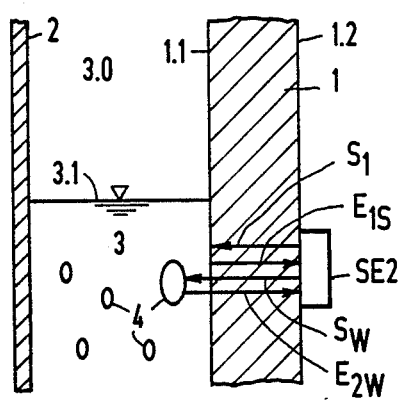
FIG 4
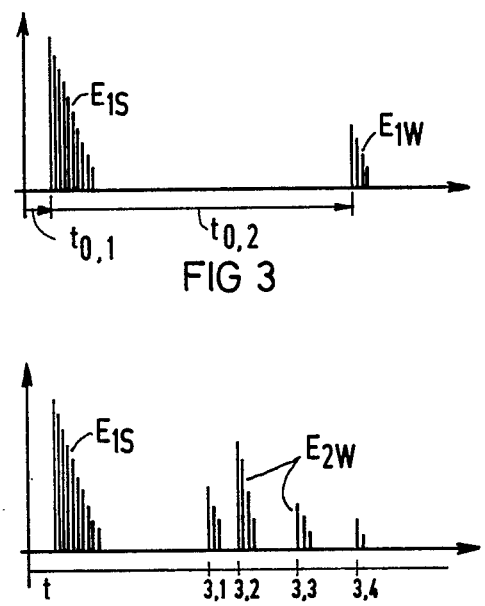
FIG 3
FIG 5
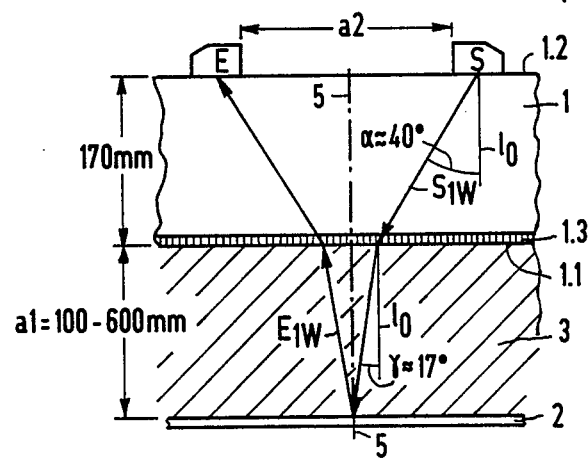
FIG 6

$\Delta_1$ : MAXIMUM FLUCTUATION WIDTH OF $U_1$
$\Delta_2$ : MAXIMUM FLUCTUATION WIDTH OF $U_2$

METHOD FOR ELECTROMAGNETIC ULTRASONIC CONVERSION FOR MONITORING THE FILL LEVEL AND BUBBLE FORMATION IN ENCLOSURES CONTAINING LIQUID

The invention relates to a method for electromagnetic ultrasonic conversion, which includes exerting dynamic-mechanical forces upon particles of an electrically conductive material of a test sample by superimposing a quasi-static magnetic field and an electromagnetic high-frequency field of a transmission converter for generating ultrasonic vibrations in a transmission process. Electrical fields are induced by means of ultrasonic waves arriving in the test sample resulting in vibrations of the particles of material inductively affecting the electromagnetic high-frequency field and the quasi-static magnetic field of a receiver converter in a receiving process. The excitation of the ultrasonic vibrations in the transmission process and the induction of electrical fields in the receiving process are effected by Lorentz forces and by magnetic forces as well as by magnetostriction forces if the test sample is made of ferromagnetic material.

A method of this kind is described in further detail in Report No. 1-84 of the Fraunhofer Institut für zerstörungsfreie Prüfverfahren [Fraunhofer Institute for Non-Destructive Testing], entitled "Ultraschallprüfung mit elektromagnetischen Wandlern" [Ultrasonic Testing with Electromagnetic Converters], by G. Hübschen, W. Repplinger and H.-J. Salzburger, pp. 23-32. Advantageous applications mentioned in this report are the testing of thick-walled components for internal flaws with free waves, described in section 4.1; the testing of the surface and the near-surface zone described in section 4.2; and the testing with guided waves (plate waves, tube waves, bar waves), described in section 4.3.

German Patent DE-PS 26 55 804 describes various embodiments of electrodynamic ultrasonic wave converters, which can function as transmission converters and/or reception converters.

In methods and apparatus of a different generic type, described in German Patent DE-PS 29 47 463 and German Published, Non-Prosecuted Application DE-OS 29 47 362, piezoelectric converters were previously used as ultrasonic transmitters and receivers for monitoring the fill level and bubble formation in containers and pipelines containing a liquid medium. These transmitters and receivers send and transmit longitudinal waves that vibrate in the direction of the width or thickness. In order to transmit this width vibration into the container or pipe wall, a medium that conducts sound, which is the so-called coupling medium, is required. The following problems arise in this process:

(a) For hot parts and sensitive surfaces that must not become wet or dirty, liquid coupling media cannot readily be used. Moreover, it must be noted that devices that guarantee constancy of the coupling over a relatively long period of time are expensive to construct, in particular with a view to retrofitting existing plants.

(b) In the case of dry coupling, a foil of silver, for instance, is placed between the sensor and the container or pipe wall. Through spring force, the sensor is then pressed against the container or pipeline. This method makes stringent demands in terms of machining of the container wall, because the container wall must be planar and sufficiently smooth in the vicinity of application of the sensor to enable good coupling. Care must also be taken to assure that the properties of the coupling foil will not change over the course of time. This method again requires a device by way of which the sensor can be pressed against the container wall, which may entail not inconsiderable difficulties in retrofitting existing plants.

It is accordingly an object of the invention to provide a method for electromagnetic ultrasonic conversion for monitoring the fill level and bubble formation in enclosures in the form of containers or pipelines containing or carrying liquid, in particular water, which overcomes the hereinaforementioned disadvantages of the heretofore-known methods of this general type and which does so without requiring liquid coupling means or the interposition of special coupling foils for coupling the ultrasonic test heads.

With the foregoing and other objects in view there is provided, in accordance with the invention, in a method for electromagnetic ultrasonic conversion, which includes exerting dynamic-mechanical forces upon particles of an electrically conductive material of a test sample by superimposing a quasi-static magnetic field and an electromagnetic high-frequency field of a transmission converter for generating ultrasonic vibrations in a transmission process, inducing electrical fields by means of ultrasonic waves arriving in the test sample resulting in vibrations of the particles of material inductively affecting the electromagnetic high-frequency field and the quasi-static magnetic field of a receiver converter in a receiving process; and effecting the excitation of the ultrasonic vibrations in the transmission process and the induction of electrical fields in the receiving process by Lorentz forces and by magnetic forces as well as by magnetostriction forces if the test sample is made of ferromagnetic material; the improvement which comprises monitoring a fill level and bubble formation in enclosure in the form of containers and pipelines having an interior for containing or carrying liquid surrounded by a wall having an inner boundary surface as well as a reflector, by coupling at least one transmission converter and at least one receiver converter to the wall, generating ultrasonic vibrations in the wall inducing ultrasonic echo signals differing by at least one of amplitude and phase in the at least one receiver converter, depending on whether the interior contains liquid, liquid containing steam or gas bubbles, or only a fluid in the form of vapor or gas, while reflecting the signals on the inner boundary surface or striking the reflector after entering the liquid and traveling a distance therein, and reflecting the signals back from the reflector through the fluid and through the wall to the receiver converter.

The advantages attainable with the invention are above all that through the use of the transmitter converter and receiver converter operating according to the principle of electromagnetic ultrasonic conversion, which can also be abbreviated as EMUS converters, the above-described coupling problems do not arise. The method of the invention makes it possible to transmit and receive ultrasound in electrically conductive materials without using coupling media and without providing for physical contact with the container wall or pipe wall.

Other features which are considered as characteristic for the invention are set forth in the appended claims.

Although the invention is illustrated and described herein as embodied in a method for electromagnetic ultrasonic conversion for monitoring the fill level and bubble formation in enclosures containing liquid, it is nevertheless not intended to be limited to the details shown, since various modifications may be made therein without departing from the spirit of the invention and within the scope and range of equivalents of the claims.

The method of operation of the invention, however, together with additional objects and advantages thereof will be best understood from the following description of specific embodiments when read in connection with the accompanying drawings.

FIG. 1 is a fragmentary, diagrammatic, cross-sectional view of a wall of a reactor pressure vessel with a water route and a built-in component functioning as a reflector, in which so-called EMUS converters, in the form of combined transmitter and receiver converters, are mounted and coupled to the outside of the container wall at two different vertical positions;

FIG. 2 is a diagram of echo height over time, showing that the ultrasonic echo signal is received in the upper transmitter-receiver converter (SE converter for short) whenever no water is present in the detected space;

FIG. 3 is a diagram similar to FIG. 2 showing a coupling signal analogous to FIG. 2, which is reflected at the inner boundary surface of the container wall, and a delayed echo signal as well, which has traveled through the water route twice and serves as a "water present" indicator;

FIG. 4 is a view similar to but modified when compared to FIG. 1, in which bubbles (vapor and/or gas bubbles) are present in the water route and only one SE converter is mounted on the outside of the container wall and coupled to the wall, in which its echo signal is changed because of the existing bubbles in the water route;

FIG. 5 is a diagram having coordinate axes corresponding to FIGS. 2 and 3, showing the echo signals received by the SE converter of FIG. 4, that is a coupling signal having the greater amplitude and a plurality of echo signals of reduced amplitude "scattered" by the bubbles, in delayed fashion;

Figure 7:
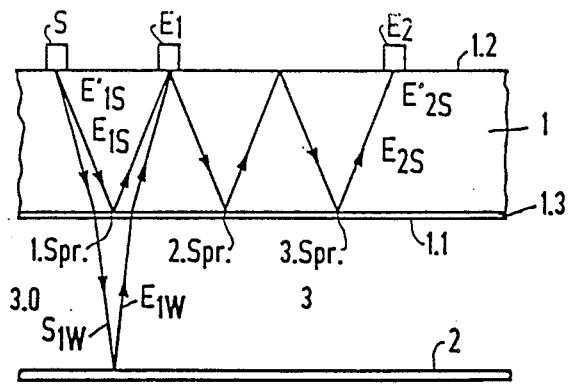
Figure 8:
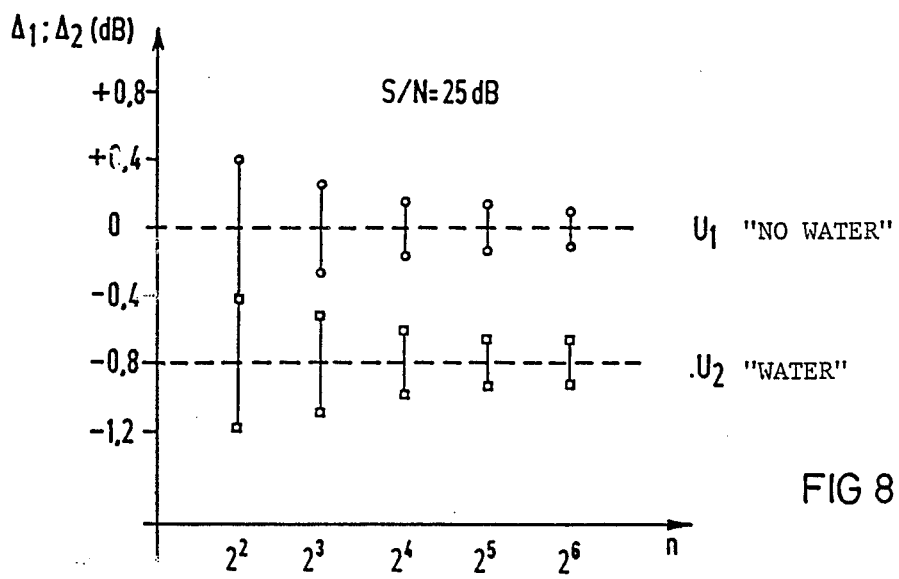
Figure 9:
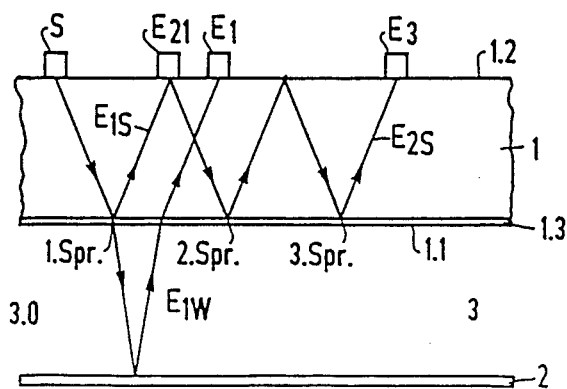

FIG. 6 is a fragmentary, cross-sectional view rotated toward the horizontal, unlike the actual conditions in use, showing the basic structure of FIGS. 1 and 4, but modified so that an inner plating of the container wall is shown as well; instead of the combined SE converter, a separate transmitter converter and receiver converter are used, which transmit vertically polarized free transversal waves, so-called SV waves, obliquely into the container wall (which applies to the transmitter converter), or receive these ultrasonic waves emerging obliquely from the container wall (which applies to the receiver converter);

FIG. 7 is a fragmentary elevational view showing a modification of the structure of FIG. 6, for illustrating a method in which the multiple total reflection at the two container wall boundary surfaces in the absence of water, and the multiple reflection at these boundary surfaces in the presence of water, are exploited, and that a plurality of receiver converters are also used to receive the multiply reflected echo signals;

FIG. 8 is a diagram showing the maximum fluctuation widths of amplitude differences of the echo signals in the "water present" and "no water present" states in dB (on the ordinate), as a function of the number n of averaged measured values, plotted on the abscissa as increasing powers of base 2;

FIG. 9 is a view similar to FIG. 7 showing a structure which is modified by providing a separate receiver converter for the echo signal traveling through the water route and for the echo signal reflected at the inner boundary surface of the container wall after the first jump, bounce or sudden change.

Referring now to the figures of the drawing in detail and first, particularly, to FIGS. 1-5 thereof, there is seen a structure through which the method of the invention is reduced to practice in a very simple manner according to a first embodiment of the invention. The physical basis of the method is explained in the above-mentioned article by G. Hübschen, W. Repplinger and H.-J. Salzburger et al in Report No. 1-84 of the Fraunhofer Institut für zerstörungsfreie Prüfverfahren [Fraunhofer Institute for Non-Destructive Testing], Saarbrücken, entitled "Ultraschallprüfung mit elektromagnetischen Wandlern" [Ultrasonic Testing with Electromagnetic Converters]. The EMUS converters (EMUS: electromagnetic ultrasonic conversion) shown in FIGS. 1 and 4 function simultaneously as transmitter and receiver converters and are therefore identified as SE1 (the upper converter in FIG. 1) and SE2 (the lower converter in FIG. 1 and the converter in FIG. 4). The converters will hereinafter be called EMUS sensors. In FIG. 1, the converters are mounted and coupled onto the outside of the container wall 1 of a pressure vessel of a nuclear reactor, in particular a boiling water reactor. Only the portion of this container wall 1 which is of interest in the present conext is shown. This also applies to a built-in wall 2 which serves as a reflector and which may, for instance, be part of a core container. The wall 2 may surround a non-illustrated fuel assembly configuration and be spaced apart by a distance $a_1$ from an inner boundary surface 1.1 of the container wall 1.

An intermediate space 3.0 between the inner surface 1.1 of the container wall and the built-in wall 2 is filled up to a liquid surface 3.1 with reactor coolant, which will hereinafter be called a water route 3.

The EMUS sensors SE1, SE2 are only diagrammatically shown in FIGS. 1 and 4 and may in principle be constructed as shown in FIGS. 4a, b, c and as described in column 5, line 66 through column 6, line 21 of German Patent DE-PS 26 55 804. In order to couple the EMUS sensors SE1, SE2, it is neither necessary to moisten the coupling surfaces nor to interpose special metal foils.

If the sensor SE2 which is the lower sensor of the EMUS sensors coupled to the container wall 1 and pressed against an outer boundary surface 1.2 of the container wall 1 by non-illustrated pressing devices in FIG. 1 is considered, then two types of echo signals are found: Echo signals of a first type $E_{1W}$, which are reflected at the built-in wall 2, travel through the water route 3 and then through the container wall 1 and thus return to the associated EMUS sensor SE2. Among these are a transmission beam $S_W$, which has been transmitted by the EMUS sensor SE2 and penetrates the container wall 1 and the water route 3 before being reflected at the built-in wall 2 and then continues its route as an echo signal of the first type. Echo signals of a second type $E_{1S}$ are the echo signals in the form of a transmission beam $S_1$ that penetrate the container wall and are directly reflected by the inside or inner boundary surface 1.1 as a signal $E_{1S}$, without penetrating the water route 3. These echo signals of the first type $E_{1W}$ are delayed on a screen with respect to a time $t=0$ by a period of time $t_{0,2}$ (which is the period from $t=0$ to t=2), and they are also reduced in amplitude, as seen by a comparison with the echo signals of the second type $I_{1S}$ in FIG. 3, in which the time delay is indicated as $t_0$, 1 and the amplitude peaks of which are higher than those of the echo signals of the first type. This is because the echo signals of the first type must travel twice through the water route 3. The echo signals of the first type $E_{1W}$ thus indicate that reactor coolant, or liquid in general, is present in the region monitored by the EMUS sensor SE2. On the other hand, the EMUS sensor SE1 located above it in FIG. 1 does not find any water route present, but finds only an air or gas space 3.0. The transmission beams S1 thereof are therefore reflected directly at the inner boundary surface 1.1 and return back to the EMUS sensor SE1 as echo signals of the second type $E_{1S}$, as also seen in FIG. 2. These signals $E_{1S}$ serve as a coupling monitor for the EMUS sensors SE1 and SE2.

The echo signals of the first type $E_{1W}$ thus serve as an indicator for the "water present" state, and the echo signals of the second type $E_{1S}$ serve as a coupling monitor. FIGS. 4 and 5 show the third basic possibility, namely the state called "water containing bubbles present". In this case, the water route 3 contains gas and/or vapor bubbles 4. If the proportion of these bubbles 4 in terms of volume is not excessively great, then a portion of the transmission beam $S_W$ passing into the water route 3 is reflected at the boundary surfaces between the water and the bubbles and reaches the EMUS sensor SE2 as an echo signal of the third type $E_{2W}$. This echo signal of the third type is also reduced in amplitude and is "scattered", as the various transit times $t_{0,3.1}$, $t_{0,3.2}$, etc, in FIG. 5 show. Tests thus far have shown that evaluatable echo signals of the third type $E_{2W}$ can still be received with an EMUS sensor if the volumetric proportion of the bubbles is not excessively great.

In the second embodiment illustrated in FIG. 6, which differs from that of FIGS. 1-5, a separate transmission converter S and receiver converter E are used as the EMUS sensors, which are disposed on the outer surface 1.2 of the container wall and are spaced apart from one another by a distance $a_2$. Therefore, the receiver converter E receives the transmitted beam $S_{1W}$, which is transmitted into the container wall 1 obliquely relative to the vertical $l_0$, as an echo signal of the first type $E_{1W}$, after its refraction at the boundary surface 1.1 and its reflection at the built-in wall 2. The angle of incidence $\alpha$ of the transmitted beam $S_{1W}$ relative to the vertical $l_0$ amounts to approximately 40° in the embodiment under discussion. The container wall 1 is also provided with a plated film on the inner surface 1.1 thereof, which thus forms the boundary surface 1.2 thereof. At this boundary surface 1.2, the transmitted beam $S_{1W}$ is refracted from the vertical $l_0$ at an angle of refraction $\gamma \approx 17°$ and then is reflected at the built-in wall 2. The echo signal of the second type $E_{1W}$ is reflected at the built-in wall 2 to the transmitted beam $S_{1W}$, in mirror inversion with respect to an axis of symmetry 5—5, it is refracted from the vertical at the boundary surface 1.2, and then reaches the receiver converter E. In the example used, the thickness of the container wall 1 was 170 mm, and the thickness $a_1$ of the water route 3 was in the range between 100 and 600 mm. The transmitted beam $S_{1W}$ of the transmitter converter S is preferably a vertically polarized free transversal wave or so-called SV wave. When a water route 3 is present, this wave is converted at the boundary surface 1.2 between the steel and the water into a longitudinal wave, which is transmitted through the water route 3 as far as the buit-in component 2. After reflection at the built-in wall 2, the longitudinal wave $E_{1W}$ is again converted at the boundary surface 1.2 into a transversal wave and then detected by the receiver converter E. This is applicable to the state "water present". If no water is present, then the above-described echo signal of the first type does not occur and only echo signals of the second type occur, which are thus reflected at the boundary surface 1.1 or are totally reflected and can be received by the receiver converter E, given sufficient surface area coverage by this converter, or by separate non-illustrated receiver converters. In the case of the state of "water containing bubbles present", the echo signal of the first type would become an echo signal of the third type, which in comparison with that of the first type would be attenuated in its amplitude and "scattered" in terms of its transit times, as has already been explained in conjunction with FIGS. 4 and 5.

It has been determined that in the case of bubble formation with a relatively high volumetric proportion, the ultrasonic signal reflected at the built-in wall or portion 2 of the container and transmitted through the water route 3 can no longer be evaluated. In order to enable replicable detection of the fill level and bubbles in this case as well, according to the third embodiment shown in FIG. 7, a transmitted signal $E_{1S}$ that is totally reflected singly and multiply at the inner and outer boundary surfaces 1.1, 1.2 of the container wall 1 is used as the echo signal of the second type, corresponding to the state "no water present", in other words a total reflection signal after the first jump, the second jump, the third jump, and so forth. Therefore, if water is absent in the space 3.0 as shown in FIG. 7, the free transversal waves of SV waves $E_{1S}$ transmitted as a transmitted beam by the transmitter converter S are multiply totally reflected at the boundary surface 1.1 and the outer boundary surface 1.2 located above it. In the illustrated embodiment, the waves are received by two receiver converters, namely $E_1$ after the first jump and $E_2$ after the third jump.

Similar to the example of FIG. 6, the echo signal of the first type $E_{1W}$, to which the transmitted beam $S_{1W}$ belongs, is also present. This echo signal of the first type arises whenever bubble-free water is present in the space 3.0. For the discussion below it is assumed that the volumetric proportion of the bubbles is relatively high, so that in this case the echo signal of the first type $E_{1W}$ disappears, and an echo signal of the third type, as explained in connection with the first and second illustrated embodiments, does not appear either. For this case, further echo signals of a fourth type are used, which are designated as $E'_{1S}$ and $E'_{2S}$.

These signals are produced from the same transmitted signals as the echo signals of the second type $E_{1S}$ and $E_{2S}$. However, they are not totally reflected echo signals but instead are signals multiply reflected at the inner and outer container wall boundary surfaces 1.1 and 1.2, or in other words reflection signals after the first jump, the second jump, the third jump, and so forth. However, because of the ensuring radiation of energy into the adjoining water route 3, with each jump they lose more energy than the totally reflected echo signals of the second type. These echo signals of the fourth type $E'_{1S}$, $E'_{2S}$, which also occur if an echo signal of the third type disappears when gas or vapor bubbles are present, are set into relation with one another and/or with the echo signals of the second $E_{1S}$ and $E_{2S}$, so that, in the absence of the echo signals of the first and third types, the amplitude differences between the echo signals of the second type and of the fourth type are an indicator for existing vapor or gas bubbles (which naturally also include air bubbles) in the water route. Accordingly, there are amplitude differences in the received signals of the receiver converters $E_1$ and $E_2$, which are received on one hand if water is present and on the other hand if no water is present. In the latter case, the amplitudes are higher, and in the first case they are lower.

As already mentioned, if there is a relatively high content of bubbles, an echo signal of the third type no longer occurs or is no longer evaluatable. In this case, it has proved to be particularly advantageous to exploit the amplitude differences between the first and the third jumps for measuring the fill level, as shown in FIG. 7. In other words, respective amplitude differences $U_1 = E_{1S}-E_{2S}$ are formed between the echo signals of the second type after the first jump $E_{1S}$ and those after the third jump $E_{2S}$. Furthermore, amplitude differences $U_2$ are formed between the echo signals of the fourth type after the first jump $E'_{1S}$ and those after the third jump $E'_{2S}$, and a level threshold is defined. If the amplitude differences $E_{1S}-E_{2S}$ is above this threshold, it serves as an indicator for the state "no water present". If an amplitude difference is below this threshold, then it relates to the difference $E'_{1S}-E'_{2S}$, and this amplitude difference serves as an indicator for the "water present" or "water containing bubbles present" state. Upon evaluation of the signal $E_{1W}$ transmitted through the water and the amplitude differences of the signals $E_{1S}$ and $E_{2S}$, or $E'_{1S}$ and $E'_{2S}$, received through the first and third jumps, the following states which can be evaluated in a receiver logic element and are shown in the table below are possible:

TABLE

| Recognition Logic for the Three Possible Operating States | |
|---|---|
| $E_{1W}$ present $E_{1S} - E_{2S}$ below threshold | water present |
| $E_{1W}$ not present $E_{1S} - E_{2S}$ below threshold | water present (but containing bubbles) |
| $E_{1W}$ not present $E_{1S} - E_{2S}$ above threshold | no water present |

In FIG. 8, the two signal levels $U_1$ (no water) and $U_2$ (water) obtained by amplitude difference formation of the echo signals after the first and third jumps are plotted as broken lines. As an example of difficult conditions, they are spaced apart by only 0.8 dB. In order to ensure that this spacing will be clearly recognizable on the screen of a cathode ray oscillograph or some other suitable measuring instrument, it is recommended that a multiplicity of individual amplitude values be averaged, and in this way the maximum fluctuation widths $\Delta_1$, $\Delta_2$, of the mean values of the received amplitudes $U_1$ for the state "no water present" and $U_2$ for the state "water present", at a given signal-to-noise ratio S/N, are reduced to minimum values, so that the amplitude difference $U_1-U_2$ to be evaluated is a multiple, for example, a multiple by a factor of 3, of the maximum fluctuation widths $\Delta_1$, $\Delta_2$, of the mean received amplitudes $U_1$, $U_2$. In the diagram of FIG. 8, it can be seen that if $64=2^6$ individual amplitude values per measured value are averaged, and if the total number of measured values is 128, the maximum fluctuation width is approximately 1% of the mean value of the measured values. In the diagram, n is the number of figures averaged.

In water routes 3 that are between 100 and 300 mm long, it is possible with the receiver $E_1$ (see FIG. 7) to receive not only the signal of the built-in component $E_{1W}$ but also the signal reflected through the first jump of an inner boundary surface 1.1 of a container, with signal-to-noise ratios of 25 to 30 dB, under normal conditions. However, dynamic losses can occur during operation. In this case, in order to obtain reliable evaluation of the amplitude difference between the "water present" and "no water present" states, an additional receiver sensor $E_{21}$ is provided for receiving the signal $E_{1S}$ as shown in FIG. 9. Accordingly, for the embodiment illustrated in FIG. 9, the echo signals of the first type $E_{1W}$ and the echo signals of the second type after the first jump $E_{1S}$ are each received by a separate receiver converter $E_1$ and $E_{21}$, especially when the water routes are long. A further receiver converter $E_3$ is then provided in order to receive the echo signals of the second type after the third jump $E_{2S}$.

Due to the two basic embodiments illustrated in FIGS. 7 and 9, in combination with the signal averaging of FIG. 8, it is possible to obtain reliable and replicable echo signals of the second and fourth type in the usual ranges of the distance between the inner boundary surface 1.1 of the container wall and the built-in wall 2, which allow a distinction to be made among the three states, "water present", "no water present", and "water containing bubbles present".

The method described above can be used not only in reactor pressure vessels, especially those of boiling water reactors, but also in pipelines carrying water or liquid, in which case the portions of the pipelines wall opposite the coupled EMUS sensors perform the function of a reflector.

The foregoing is a description corresponding in substance to German Application P 37 32 219.2, dated Sept. 24, 1987, the International priority of which is being claimed for the instant application, and which is hereby made part of this application. Any material discrepancies between the foregoing specification and the aforementioned corresponding German application are to be resolved in favor of the latter.

We claim:

1. In a method for electromagnetic ultrasonic conversion, which includes exerting dynamic-mechanical forces upon particles of an electrically conductive material of a test sample by superimposing a quasi-static magnetic field ($B_O$) and an electromagnetic high-frequency field (B) of a transmission converter for generating ultrasonic vibrations in a transmission process, inducing electrical fields by means of ultrasonic waves arriving in the test sample resulting in vibrations of the particles of material inductively affecting the electromagnetic high-frequency field (B) and the quasi-static magnetic field ($B_O$) of a receiver converter in a receiving process; and effecting the excitation of the ultrasonic vibrations in the transmission process and the induction of electrical fields in the receiving process by Lorentz forces ($F_L$) and by magnetic forces ($F_M$) as well as by magnetostriction forces ($F_{MS}$) if the test sample is made of ferromagnetic material;

the improvement which comprises monitoring a fill level and bubble formation in a cylindrical reactor pressure vessel of a nuclear power plant having an interior (3.0) for containing reactor coolant water having a normal fill level and following a water route (3) adjacent a wall (1) having an inner boundary surface (1.1) as well as a reflector (2) in the form of a built-in component within the water route, by coupling at least one transmission converter (SE1, SE2, S) from outside onto the wall at least at one location just below the normal fill level and by coupling at least one receiver converter (SE1, SE2, E, $E_1$, $E_2$, $E_{21}$, $E_3$) to the wall (1), generating ultrasonic vibrations in the wall inducing ultrasonic echo signals differing by at least one of amplitude and phase in the at least one receiver converter (SE1, SE2, E, $E_1$, $E_2$, $E_{21}$, $E_3$), depending on whether the interior (3.0) contains liquid (3), liquid (3) containing steam or gas bubbles (4), or only a fluid in the form of vapor or gas, while reflecting the signals on the inner boundary surface (1.1) or striking the reflector (2) after entering the liquid (3) and traveling a distance therein, and reflecting the signals back from the reflector through the fluid (3) and through the wall (1) to the receiver converter (SE1, SE2, E, $E_1$, $E_2$, $E_{21}$, $E_3$), returning the ultrasonic transmitted beam ($S_W$, $S_{1W}$) traveling through the container wall (1) as well as the adjacent water route (3) of the reactor water and striking the built-in component (2) to the outside (1.2) of the container wall (1) in the form of an echo signal of a first type ($E_{1W}$) where it is received as a "water present" signal by a receiver converter (SE1, SE2, E), while reflecting the transmitted beam ($S_1$) on the inside (1.1) of the container wall (1) where it is received as an echo signal of a second type ($E_{1S}$) at the receiver converter or at another receiver converter as a "no water present" signal, in the absence of water, the echo signal of the second type ($E_{1S}$) having a shorter transit time and a greater amplitude than the echo signal of the first type ($E_{1W}$)

converting the "water present" echo signal of the first type to a "water containing bubbles present" echo signal of a third type ($E_{2W}$) being scattered into a plurality of partial echo signals and reduced in amplitude, if vapor or gas bubbles (4) are present in the monitored water route (3) up to a threshold of the bubble volume proportion, transmitting vertically polarized free transversal or SV waves inward at an oblique angle ($\alpha$) relative to an incident vertical ($1_0$) with the at least one transmitter converter (S), refracting the obliquely transmitted beam ($S_{1W}$) toward the vertical at the boundary surface (1.1) of the container wall and the water route, and converting the transmitted beam into a longitudinal wave being reflected at the built-in component (2), traveling once again through the boundary surface (1.1) between the water route and the container wall and then being converted back into an SV wave and refracted back toward the vertical and received as an echo signal of the first or third type ($E_{1W}$ or $E_{2W}$) by the receiver converter (E), the transmitted beam being distinguished in terms of amplitude and phase from the echo signal of the second type ($E_{1S}$), which is totally reflected at the inner boundary surface (1.1) of the container wall (1) and from there reaches the receiver converter (E) unrefracted, in the absence of water.

2. Method according to claim 1, wherein the reactor pressure vessel is a pressure vessel of a boiling water reactor.

3. Method according to claim 1, wherein the vessel wall has an outer boundary surface (1.2), the method further comprises providing the echo signal of the second type corresponding to the "no water present" state in the form of a transmitted signal ($E_{1S}$, $E_{2S}$, ...) reflected singly and multiply at the inner and outer boundary surfaces (1.1, 1.2) of the vessel wall (1), as a total reflection signal after a first jump, a second jump, and a third jump, etc., providing further echo signals of a fourth type in addition to the echo signals of the first type which correspond to the "water present" state and include the transmitted signals ($E_{1W}$) reflected at least once at the built-in component and passing through the water route twice, producing the echo signals of the fourth type from transmitted signals reflected singly and multiply at the inner and outer surfaces of the vessel wall, representing reflection signals after the first jump, the second jump, and the third jump, etc, the echo signals of the fourth type losing more energy with each jump than the totally reflected echo signals of the second type because of the ensuing emission of energy into the adjoining water route, the echo signals of the fourth type ($E'_{1S}$, $E'_{2S}$) also occurring whenever an echo signal of the third type disappears, in the presence of gas or vapor bubbles, the echo signals of the fourth type being set into relation with at least one of the other echo signals of the fourth type and the echo signals of the second type, and using the amplitude differences between the echo signals of the second and fourth types as an indicator of existing vapor or gas bubbles in the water route, in the absence of the echo signals of the first and third types.

4. Method according to claim 3, which comprises detecting the fill level and bubbles in the presence of higher proportions of bubbles by volume.

5. Method according to claim 3, which comprises forming amplitude differences ($U_1 = E_{1S} - E_{2S}$) between the echo signals of the second type after the first jump and those after the third jump, and forming amplitude differences ($U_2 = E'_{1S} - E'_{2S}$) between the echo signals of the fourth type after the first jump and those after the third jump, defining a level threshold with amplitude differences ($E_{1S}$-$E_{2S}$) above the threshold as an indicator for the state "no water present", and defining a level threshold with amplitude differences ($E'_{1S}$-$E'_{2S}$) below the threshold as an indicator for the state "water present" or "water containing bubbles present".

6. Method according to claim 3, which comprises averaging a great number of individual amplitude values in order to evaluate small amplitude differences, for reducing maximum fluctuation widths ($\Delta_1$, $\Delta_2$) of mean values of the received amplitudes ($U_1$) for the "no water present" state and ($U_2$) for the "water present" state at a given signal-to-noise ratio (S/N) to minimum values, and setting the amplitude difference ($U_1$-$U_2$) to be evaluated at a multiple of the maximum fluctuation widths ($\Delta_1$, $\Delta_2$) of the mean received amplitudes ($U_1$, $U_2$).

7. Method according to claim 3, which comprises receiving each of the echo signals of the first type ($U_{1W}$) and the echo signals of the second type after the first jump ($E_{1S}$) with a separate receiver converter ($E_1$ or $E_{21}$), and receiving the echo signals of the second type after the third jump ($E_{2S}$) with a further receiver converter ($E_3$).

8. Method according to claim 7, which comprises receiving the echo signals after long water routes.

9. Method for monitoring fill level and bubble formation through electromagnetic ultrasonic conversion in a cylindrical boiling water reactor pressure vessel of a nuclear power plant having an interior (3.0) for containing reactor coolant water having a normal fill level and following a water route (3) adjacent a wall (1) having an inner boundary surface (1.1) as well as a reflector (2) in the form of a built-in component within the water route, which comprises coupling at least one transmission converter (SE1, SE2, S) from outside onto the wall at least at one location just below the normal fill level, coupling at least one receiver converter (SE1, SE2, E, $E_1$, $E_2$, $E_{21}$, $E_3$) to the wall (1), generating ultrasonic vibrations in the wall inducing ultrasonic echo signals differing by at least one of amplitude and phase in the at least one receiver converter (SE1, SE2, E, $E_1$, $E_2$, $E_{21}$, $E_3$), depending on whether the interior (3.0) contains liquid (3), liquid (3) containing steam or gas bubbles (4), or only a fluid in the form of vapor or gas, while reflecting the signals on the inner boundary surface (1.1) or striking the reflector (2) after entering the liquid (3) and traveling a distance therein, and reflecting the signals back from the reflector through the fluid (3) and through the wall (1) to the receiver converter (SE1, SE2, E, $E_1$, $E_2$, $E_{21}$, $E_3$), returning the ultrasonic transmitted beam ($S_W$, $S_{1W}$) traveling through the container wall (1) as well as the adjacent water route (3) of the reactor water and striking the built-in component (2) to the outside (1.2) of the container wall (1) in the form of an echo signal of a first type ($E_{1W}$) where it is received as a "water present" signal by a receiver converter (SE1, SE2, E), while reflecting the transmitted beam ($S_1$) on the inside (1.1) of the container wall (1) where it is received as an echo signal of a second type ($E_{1S}$) at the receiver converter or at another receiver converter as a "no water present" signal, in the absence of water, the echo signal of the second type ($E_{1S}$) having a shorter transit time and a greater amplitude than the echo signal of the first type ($E_{1W}$), and converting the "water present" echo signal of the first type to a "water containing bubbles present" echo signal of a third type ($E_{2W}$) being scattered into a plurality of partial echo signals and reduced in amplitude, if vapor or gas bubbles (4) are present in the monitored water route (3) up to a threshold of the bubble volume proportion.

10. Method for monitoring fill level and bubble formation through electromagnetic ultrasonic conversion in a cylindrical boiling water reactor pressure vessel of a nuclear power plant having an interior (3.0) for containing reactor coolant water having a normal fill level and following a water route (3) adjacent a wall (1) having an inner boundary surface (1.1) as well as a reflector (2) in the form of a built-in component within the water route, which comprises coupling at least one transmission converter (SE1, SE2, S) from outside onto the wall at least at one location just below the normal fill level, coupling at least one receiver converter (SE1, SE2, E, $E_1$, $E_2$, $E_{21}$, $E_3$) to the wall (1), generating ultrasonic vibrations in the wall inducing ultrasonic echo signals differing by at least one of amplitude and phase in the at least one receiver converter (SE1, SE2, E, $E_1$, $E_2$, $E_{21}$, $E_3$), depending on whether the interior (3.0) contains liquid (3), liquid (3) containing steam or gas bubbles (4), or only a fluid in the form of vapor or gas, while reflecting the signals on the inner boundary surface (1.1) or striking the reflector (2) after entering the liquid (3) and traveling a distance therein, reflecting the signals back from the reflector through the fluid (3) and through the wall (1) to the receiver converter (SE1, SE2, E, $E_1$, $E_2$, $E_{21}$, $E_3$), returning the ultrasonic transmitted beam ($S_W$, $S_{1W}$) traveling through the container wall (1) as well as the adjacent water route (3) of the reactor water and striking the built-in component (2) to the outside (1.2) of the container wall (1) in the form of an echo signal of a first type ($E_{1W}$) where it is received as a "water present" signal by a receiver converter (SE1, SE2, E), while reflecting the transmitted beam ($S_1$) on the inside (1.1) of the container wall (1) where it is received as an echo signal of a second type ($E_{1S}$) at the receiver converter or at another receiver converter as a "no water present" signal, in the absence of water, the echo signal of the second type ($E_{1S}$) having a shorter transit time and a greater amplitude than the echo signal of the first type ($E_{1W}$), and converting the "water present" echo signal of the first type to a "water containing bubbles present" echo signal of a third type ($E_{2W}$) being scattered into a plurality of partial echo signals and reduced in amplitude, if vapor or gas bubbles (4) are present in the monitored water route (3) up to a threshold of the bubble volume proportion, transmitting, vertically polarized free transversal or SV waves inward at an oblique angle ($\alpha$) relative to an incident vertical ($l_0$) with the at least one transmitter converter (S), refracting the obliquely transmitted beam ($S_{1W}$) toward the vertical at the boundary surface (1.1) of the container wall and the water route, and converting the transmitted beam into a longitudinal wave being reflected at the built-in component (2), traveling once again through the boundary surface (1.1) between the water route and the container wall and then being converted back into an SV wave and refracted back toward the vertical and received as an echo signal of the first or third type ($E_{1W}$ or $E_{2W}$) by the receiver converter (E), the transmitted beam being distinguished in terms of amplitude and phase from the echo signal of the second type ($E_{1S}$), which is totally reflected at the inner boundary surface (1.1) of the container wall (1) and from there reaches the receiver converter (E) unrefracted, in the absence of water.

* * * * *